United States Patent [19]

Zeller et al.

[11] Patent Number: 4,659,390
[45] Date of Patent: Apr. 21, 1987

[54] METHOD AND MANUFACTURE FOR MOISTURE-STABLE, INORGANIC, MICROPOROUS SACCHARIDE SALTS

[75] Inventors: Bary L. Zeller, Pleasantville, N.Y.; Randal P. McKay, Paramus, N.J.; Fouad Z. Saleeb, Pleasantville, N.Y.

[73] Assignee: General Foods Corporation, White Plains, N.Y.

[21] Appl. No.: 674,626

[22] Filed: Nov. 26, 1984

Related U.S. Application Data

[63] Continuation-in-part of Ser. No. 401,767, Jul. 26, 1982, abandoned.

[51] Int. Cl.$^4$ .............................. C13F 1/00; C13F 3/00
[52] U.S. Cl. ...................................... 127/29; 127/46.1; 426/385; 426/658; 536/124
[58] Field of Search .................... 127/29, 46.1, 47, 58, 127/61, 30; 536/1.1, 123, 121, 124, 126; 34/5; 426/385, 658

[56] References Cited

U.S. PATENT DOCUMENTS

| | | | |
|---|---|---|---|
| Re. 28,781 | 4/1976 | Konig et al. | 536/121 X |
| 1,807,608 | 6/1931 | Stern | 536/121 |
| 1,850,036 | 3/1932 | Steffen | 536/121 X |
| 3,692,766 | 9/1972 | Reinicke et al. | 536/121 |
| 3,922,369 | 11/1975 | Glicksman et al. | 426/548 |
| 4,142,916 | 3/1979 | Ogasa et al. | 127/63 |
| 4,211,015 | 7/1980 | Adams et al. | 34/5 |
| 4,237,147 | 12/1980 | Merten et al. | 426/590 |
| 4,263,052 | 4/1981 | Bichsel et al. | 127/41 |
| 4,389,422 | 6/1983 | Hudak | 426/424 X |
| 4,396,763 | 8/1983 | Tsuchiya et al. | 536/123 |
| 4,435,389 | 3/1984 | Mutai et al. | 536/123 X |
| 4,541,873 | 9/1985 | Scheuz et al. | 127/46.1 |

FOREIGN PATENT DOCUMENTS 2071104 9/1981 United Kingdom .

*Primary Examiner*—Richard V. Fisher
*Assistant Examiner*—W. Gary Jones
*Attorney, Agent, or Firm*—Thomas R. Savoie; Daniel J. Donovan; Thomas A. Marcoux

[57] ABSTRACT

The present invention provides a method for complexing a metal cation and a saccharide to form thereby a cation-saccharide salt. Upon instantly solidifying and dehydrating particles of said cation-saccharide compound, a highly microporous material results, said material being capable of adsorbing large volumes of volatile flavor/aroma or gaseous compounds.

16 Claims, No Drawings ized, cation-saccharide salts, said salts being capable of adsorbing significant amounts of volatile aroma and flavor components. Fashioned from almost any saccharide or mixture of saccharides, the salts of this invention are essentially amorphous in nature. The salts present no defined crystalline lattice and are composed of an inorganic cation chemically bonded to one or more saccharide units. The product, formed thereby may be constructed from such recalcitrant sugars as fructose and glucose, and with its excellent flow properties, may be easily added to dried food and beverage mixes.

Another object of the present invention is to provide a method for instantaneously freezing and thereafter freeze-drying a saccharide at a temperature significantly above its known collapse temperature to preserve the

METHOD AND MANUFACTURE FOR MOISTURE-STABLE, INORGANIC, MICROPOROUS SACCHARIDE SALTS

This application is a continuation-in-part of our copending U.S. application, Ser. No. 401,767, filed July 26, 1982 and now abandoned.

BACKGROUND OF THE INVENTION

The present invention relates to edible microporous materials, and more specifically, to a method for the manufacture of a microporous, inorganic, essentially non-hygroscopic, cation-sugar salt which is capable of adsorbing large volumes of diverse flavor and aroma components or gases, such as carbon dioxide.

In the area of prepared foods, there is a basic need to offer a packaged food or drink product, that is attractive to the various senses of the mature consumer. With the purchase of the product, the first barrier is overcome. Opening the container or jar is usually the next preparatory step that the consumer undertakes. The packaging and retention of food products within a closed container presents unique problems to the manufacturer. Greeting the consumer's olfactory senses is the "headspace" aroma, said aroma comprising volatile components which hang suspended in the void between the jar cap and the dried mix. Upon receiving the aroma via olfactory receptors, the consumer arrives at a perception of whether or not the product contained therein is fresh and potentially attractive to the taste. In fact, freshness and taste quality may not consistently be ascertained in this manner. Therefore, it is imperative that an intensely pleasant yet familiar aroma wafts up to the consumers' olfactory senses, regardless of the length of time that the product has endured storage. After a portion has been extracted from the container or jar, the container is resealed, only to be reopened for a second test of product acceptability. When the consumer opens the container for the second time, he or she expects to be met by the same pleasant and familiar aroma that was perceived in the first instance. Hence, the "headspace aroma", the aroma suspended within the air space beneath the jar cap of a dried food or drink mix, is still of strategic import; if there is no aroma, then there is a supposition that the product has become stale. Such a misperception often militates against the repurchase of the product by the consumer. The desired presence of a headspace aroma with each successive opening of the jar, commonly referred to as an in-use headspace aroma, can only exist if the aroma source does not release all sorbed aroma at one time.

A second expected quality of dried food or drink mixes is that said mixes provide a well rounded flavor when reconstituted with water. Often the process of preparing the dried product removes the deeper tones from the comestible, making the product organoleptically unsatisfactory. Moreover, it is often difficult to load the dried mix with flavor components, since these components are often volatile and are lost when the container is repeatedly opened. Again, as with aroma, the consumer is stereotypically fixated on certain flavors that have become familiar to him or her. And again, if the expectation of experiencing the characteristic flavor is not realized by the consumer, negative feelings will accrue with adverse effects upon the continued purchase of the product. Therefore, there has been a long standing need for an easily added edible carrier that can actively adsorb large quantities of volatile flavor and aroma components so that said components can be releasibly held, so that when the product is reconstituted or when the container is opened said components will be liberated via controlled release.

The use of edible "microporous" material as sorbents for gases and aromatic volatile has been disclosed in U.S. Pat. No. 4,389,422 to Hudak and a related patent disclosures such as Canadian Pat. No. 1,142,018 to Hudak and Saleeb. The fomation of "microporous" sucrose particles has been disclosed in filed U.S. patent application, Ser. No. 375,052 filed May 5, 1982. These sucrose particles have, however, been found to be hygroscopic and to quickly loose porosity upon exposure to the atmosphere.

Microporous or highly porous sorbents possess a relatively large surface area in excess of ten square meters per gram and also possess a large number of pores within the range of 10 to 20 angstroms in radius. These particles rely on their internal pore structure to provide such large surface areas as, by way of illustration, cubic particles of sodium chloride having a side dimension as small as one micron would only provide a geometric or external surface area of 2.8 $m^2/g$ (reference: Adamson, *Physical Chemistry of Surfaces*, p. 247, Interscience Publishers, Inc., 1960). Microporous particles will evidence a phenomenon known as capillary condensation in which liquids condense within the 10 to 250 angstrom pores at vapor pressures significantly below saturation.

U.S. Pat. No. 4,263,052 to Bicksel et al. teaches that a "sugar-salt" complex may be formed although the product would not be microporous; the method described therein teaches a method for deriving a crystalline form of fructose of high purity.

U.S. Pat. No. 4,237,147 to Merten et al. teaches a method for forming an amorphous calcium carbonate complex which readily releases carbon dioxide on acid hydrolysis.

Of interest is British Pat. No. 2,071,104 issuing to Koshida et al., said reference teaching the formation of porous saccharide granules. The essentially crystalline composition is macro-porous and the potential constituents exclude such saccharides as fructose or glucose.

Heretofore there has not been a successful attempt to create microporous glucose or fructose sorbents or moisture-stable sucrose sorbents to adsorb gaseous components therein.

SUMMARY OF THE INVENTION

It is an object of the present invention to provide a method for manufacturing inorganic, microporous, essentially non-hygroscopic, easily-solubil microporous structure created by the fine ice crystals generated during the freezing step.

Yet another object of the present invention is to produce an inorganic cation-saccharide salt that has a high surface area within the micropores, so that said surface area is equal to or greater than 10 $m^2/g$.

Still another object of the present invention is to present a material that can adsorb significant amounts of volatile flavor and aroma molecules so that the consumer will perceive a desirable headspace odor when the cap or container lid is removed from the container. A correlative object is to provide a microporous material wherein large volumes of carbon dioxide may be adsorbed so that said cation-saccharide salt may provide a source of carbonation, when dissolved in aqueous beverages.

Accordingly, to effect the manufacture of the desired microporous cation-saccharide salt, the following methodology is to be operatively employed. An inorganic cation-containing compound which will, upon dissolution in water, raise the pH of the aqueous solution to above pH 9 is dissolved in water. A water-soluble saccharide is also dissolved in the pH-elevated aqueous solution. The compound that is formed by the combining of the liberated cation with one or more saccharide units is to be described as a cation-saccharide salt, which has different colligative properties when compared to the starting saccharide material in aqueous solutions. To effect the formation of a cation-saccharide salt possessing a microporous structure, the solution is quickly frozen and dehydrated via the techniques elucidated herein below.

This highly microporous structure allows the user to load the cation-saccharide salt with aroma or flavor components as well as with gases like carbon dioxide, said components being released when said cation-saccharide salt is reconstitutedly dissolved in an aqueous system or when the loaded cationsaccharide salt is exposed to an atmosphere wherein the partial pressure of the sorbed volatiles causes desorption.

Other objects and advantages of the present invention shall be evident to one skilled in the art when reference is taken to the detailed description that follows.

DETAILED DESCRIPTION OF PRESENT INVENTION

Among the methods for producing the non-hygroscopic, microporous inorganic salts from water soluble saccharides is to form a solution containing a dissolved saccharide and sufficient dissolved and dissociated inorganic cation-containing basic compound to produce a pH of at least 9.0. The thus formed solution is then sprayed, preferably as a finely atomized spray, into a cryogenic fluid or a cold dehydrating solvent. In both cases the spray droplets are solidified in the fluid or solvent, thereafter separated from the fluid or solvent and then dried under conditions which will avoid collapse of the microporous structure contained in the solidified and dried droplets. The resulting particles are highly microporous and stable at ambient humidities. These particles may be easily introduced via existing machinery to a dried mix without the need for altering said machinery. The particles consist essentially of a cation-saccharide salt which is soluble in an aqueous medium. Furthermore, the particles possesses a microporosity, as measured by its surface area, which exceeds values heretofore available in saccharide materials. Accordingly to this invention saccharide materials which have a surface area exceeding a lower limit of 10 $m^2/g$, preferably 60 $m^2/g$, and which contain a large quantity of pores having a radius of less than 150 angstroms may be produced. By employing the method as disclosed hereinbelow, surface areas of over 200 $m^2/g$, with pore volumes in excess of 50 to 500 microliters per gram can be achieved in sugars, such as fructose and sucrose, that have not been made microporous previously.

As a preferred embodiment an inorganic compound for example, calcium oxide, is added to an aqueous medium, said aqueous medium being essentially comprised of water. Any metal cation compound capable of raising the pH of an aqueous solution to a level of 9.0 or above may be adaptively substituted. Calcium compounds like calcium oxide or calcium hydroxide are peculiarly adapted to food uses in general and to dried drink mixes in particular. Therefore, examples will be drawn using these compounds. Upon reconstitution, citric acid, which is a major constituent in many drink mixes, combines with the calcium ion of the calcium-saccharide salt thereby forming calcium citrate. Calcium citrate harmoniously combines with most drink or dried food mixtures. The saccharide component of the cationsaccharide salt is liberated, and flows into the aqueous system of the dissolved mix imparting additional sweetness to the final product. A great variety of inorganic compounds may be used to fashion microporous materials, for example, the cation liberated from the inorganic compound may be monovalent, divalent or trivalent in nature. The ramifications of this substitional phenomena will become apparent later.

According to the preferred embodiment of this invention which utilizes calcium oxide as the inorganic compound, the first step is to suspend the calcium oxide in the aqueous system. The initial solvation of the calcium oxide results in the liberation of calcium cations, $Ca^{++}$ and the generation of hydroxyl anions, $OH^-$. The pH of the solution rises. A saccharide is then added to the aqueous solution. The saccharide is preferably a mono or dissaccharide; however, polysaccharides or mixtures of mono, di and polysaccharides are within the scope of this invention. The ionization of the calcium oxide raises the pH of the aqueous solution, and a pH of at least 9 facilitates the reaction and the formation of the products. Alternatively, one may dissolve the desired saccharide or combinations of saccharides in the aqueous system and then add the inorganic compound.

The chemical reaction mechanism resulting in the creation of the calcium-saccharide salt involves the addition of a strong base, such as calcium oxide, to saccharide (a weak acid) in aqueous solution. The strong base raises the pH of the aqueous solution and encourages the ionization of the saccharide. The hydroxyl groups of the saccharide molecules are natural areas for removal of a $H^+$ ion. Thus liberated, the $H^+$ ions from the saccharide combine with the hydroxyl ($OH^-$) ions which arise by virtue of the increase in pH generated by the suspended calcium oxide. The removal of a hydrogen from the hydroxyl group of the saccharide causes a negative charge to develop on one or more of the hydroxyl groups of said saccharide. With removal of the hydrogen from a hydroxyl group of the saccharide, calcium or another cation is able to bond with the unencumbered oxygen. Therefore, if one has a solution wherein a number of mono, di or polysaccharides are present, a calcium ion will be able to link two saccharides allowing for a new compound, an inorganic cation-saccharide salt to develop. The new compounds have been found to possess a higher molecular weight than the starting saccharide, are not sweet in taste, and are insoluble in alcohol.

As an alternate to calcium oxide, such trivalent metal cations as aluminum could link up to three saccharide molecules. As a basic rule, by elevating the pH of the aqueous solution, a favorable environment for saccharide ionization is offered, and the formation of the cation-saccharide salt may easily occur.

It should be noted that the source of the liberated cation is derived from the dissolution of an inorganic compound in an aqueous system. The anion should preferably be either an oxide, a hydroxide or a carbonate. Suitable monovalent cations are lithium (Li), sodium (Na), potassium (K), rubidium (Rb) or cesium (Cs), said monovalent cations complexing with a single saccharide. Useful divalent cations, which will link two saccharides, include magnesium (Mg), calcium (Ca), zinc (Zn), strontium (Sr) and barium (Ba). Finally, suitable trivalent cations are aluminum (Al), cerium (Ce) and lanthanum (La). It has been found that the use of trivalent cations alone is not desirable and that some monovalent or divalent cations should also be present. It has also been found that when the saccharide consists of monosaccharides it is preferable to avoid using exclusively monovalent cations.

It has been found that a preferred mole ratio range may be established, reflecting a value where the greatest number of saccharide molecules will be linked with the liberated cations. For example, for divalent cations, a mole ratio range of about 0.5–1.5 moles of free cation to 1 mole of saccharide will encourage the most efficient salt formation to occur. Exceeding the upper mole limit will merely result in an excess of cations which will not contribute to further inter-molecular linking.

Following the formation of the saccharide salt, the next logistical step is the separation of the newly formed compound from the solution. The separation method, by necessity must assure the generation and preservation of a highly microporous structure in the dehydrated product. The preferred separation technique of this invention is one wherein the aqueous cation-saccharide salt solution is transferred to a spraying apparatus wherein said solution is atomized therethrough creating very fine droplets. By spraying the solution via a high pressure hydraulic nozzle, that is, a nozzle of low capacity and high pressure, atomization of the solution is effected. The spray from the hydraulic nozzle is received in a liquid cryogen having a temperature below $-100°$ C., as for example liquid nitrogen, and is thereby instantly frozen. Generation of the micropores is achieved by forming microporous-sized ice crystals as a result of the instantaneous freezing and thereafter removing the ice in a manner which does not permit collapse of the micro-structure. Removal of the ice crystals such as by freeze-drying may be done at a temperature which is significantly above the collapse temperature of the saccharide compound by itself.

Spraying of the cation-saccharide salt solution into a frigid dehydrating, preferably anhydrous, solvent is an alternate separation media which not only preserves the cation-saccharide salt, but also induces formation of a microporous structure in the dehydrated salt particles. The dehydrating solvent such as methanol, but preferably ethanol, should be maintained at around $-60°$ C. or below to solidify the spray particles. The cation-saccharide salt which is not soluble in alcohols, is dehydrated by having the water leached out from the insoluble salt structure. After separating the dehydrated particles from the subambient solvent, the particles should be washed with the solvent to remove the last bit of water so that upon a rise in temperature no meltback or dissolution occurs. The resultant washed particles are then placed in a vacuum oven to remove the solvent. The resultant microporous particles are essentially non-hygroscopic and will accept, via adsorption, desired gaseous components.

The newly-formed, inorganic cation-saccharide salt displays colligative characteristics which do not properly characterize the individual saccharide component or cation component. For example, the freezing characteristics of the newly formed compounds exhibit at least a 10° C. increase in the collapse temperature, suggesting that a unique, larger molecule has been formed. Moreover, the dried cation-saccharide material displays a unique yet slight coloration, suggestive of an ionic reaction having taken place. It appears that by elevating the pH, which causes the ionization of the hydroxyl group of the saccharide, "side" reactions of the keto-enol type take place. These "side" reactions are probably responsible for the slight change of color found in the formed saccharide salt. In the calcium-fructose salt, the microporous particles exhibit a yellow cast, thereby coloring what was once a white material.

By reference to EDAX photographs (EDAX a Registered Trademark of EDAX International Inc. and applied to the EDAX 9100 Energy Dispersive X-Ray Analysis Systems) it has been determined that the compounds formed in accordance with this invention are constructed via the reaction of the inorganic compound and the saccharide. By employing the EDAX system, an instrument and procedure closely related to the scanning electron microscope, one may obtain structural and chemical information about the newly-formed material, and via amplification, convert the energy into electrical signals so that a qualitative reading may be obtained. Therefore, in the instant invention, the EDAX system has been used to qualitatively support the existence of the cation within the structure of the newly-formed compound. Thus, EDAX photographs depict the presence of calcium in the compound formed by reacting fructose and calcium oxide, the presence of calcium in a compound formed by reacting glucose and calcium oxide, and the presence of calcium in a compound formed by reacting sucrose and calcium oxide.

The microporous particles of this invention are useful to sorb aromatic and/or flavorful volatiles at a level of from 0.1% to 20% by weight. The volatile-loaded particles may be readily combined, as by dry-blending, with powdered, low-aroma food products such as beverage mixes typically at a level of from 0.05 to 2.0%, preferably at from 0.1 to 1% by weight. Typically aromatic or other gases will be loaded at a level between about 0.1% to 3% by weight. Aromatic materials such as flavor oil may be loaded in the microporous particles at considerably higher levels. The methods of contacting the microporous particles with volatiles or gases for the purpose of loading the particles can be many and varied. Such methods are known to the art as illustrated by the aforementioned Hudak patent which is hereby incorporated by reference.

The newly-formed microporous material may be advantageously employed to sorb great quantities of carbon dioxide or other commercially desirable gases. In the case of calcium-sugar microporous salts, a second volume is chemically held within said compound in the form of a non-crystalline carbonate.

EXAMPLE 1

Three aqueous sugar solutions (sucrose, glucose, fructose) having a soluble solids concentration of 25% by weight, were prepared by reconstituting 20 g of the pure sugars in 60 ml of water. These solutions were sprayed in open vessels containing liquid nitrogen. The fine droplets (less than 200 microns) were immediately frozen and dispersed in the cryogen. All three solutions were sprayed by means of a high-pressure, low-capacity hydraulic nozzle (obtained from Spray Systems Inc.) using nitrogen gas as the pressurizing fluid. In each case the liquid nitrogen and frozen particle mixture was poured into freeze-drying trays. The trays were transferred to the freeze-drying chamber and placed on the already chilled −40° C. freeze drier shelves. The liquid nitrogen was allowed to boil off leaving behind a flat bed of frozen sphericle particles having a nominal bed depth of ⅛ to ¼ inches. The freeze drier chamber was sealed and the trays were subjected to a vacuum of 10 microns of Hg and an initial shelf temperature of −30° C. for a period of 4 hours, −25° C. for a period of 16 hours, −20° C. for 4 hours, −10° C. for a period of 4 hours, 0° C. for a period of 16 hours, 5° C. for a period of 4 hours, 25° C. for 4 hours. The vacuum in the freeze drier chamber was broken with the admission of dry air. The contents of the individual trays were transferred to separate jars which were kept in a moisture-free environment. The fructose sample upon retrieval from the freeze drier was observed to be a highly viscous liquid syrup. The freeze dried glucose particles took on the appearance of a dry powder but readily aggregated and later collapsed (1 day) in storage to form a syrup. Only the freeze dried sucrose was a dry, free-flowing powder and this powder was found to possess a microporous structure having a $N_2$ surface area of about 96 $m^2/g$ (determination based on nitrogen adsorption isotherm analysis).

EXAMPLE 2

An aqueous potassium-fructose solution having a cation to sugar mole ratio of approximately 1:1 and a total solids concentration of 33% by weight was prepared by dissolving 20 grams of fructose in 58.7 mls of 2.1 N KOH solution.

The potassium-fructose mixture or solution thereof was sprayed under 1000 psi through a high pressure, low capacity, hydraulic nozzle into an open insulated vessel containing liquid nitrogen. The fine droplets of solution were instantaneously frozen and dispersed in the liquid cryogen. The liquid nitrogen and frozen particle mixture was poured into freeze-drying trays. The trays were transferred and the sample was freeze dried in accordance with the steps outlined in Example 1.

The freeze dried potassium-fructose sample was observed to be a dry, free-flowing powder which did not readily aggregate and nitrogen adsorption isotherm analysis indicated that these particles were microporous and had a surface area of approximately 18 $m^2/g$.

EXAMPLE 3

An aqueous calcium-fructose solution having a cation to sugar mole ratio of approximatly 1:1 and a total solids concentration of 25% by weight was prepared by adding 6.23 g of CaO to an aqueous fructose solution which was prepared by dissolving 20 grams of fructose in 78.7 mls of deionized water. The solution was continuously stirred until the pale yellow solution cleared. The calcium-fructose solution was sprayed, frozen, transferred, and freeze dried as per the steps outlined in Example #1.

The resultant freeze dried calcium-fructose particles were observed to be dry, free-flowing powders and later found to be non-hygroscopic microporous solids having $N_2$ surface area of 144 $m^2/g$.

EXAMPLE 4

The addition of 20 grams of fructose to a CaO suspension which was prepared by adding 4.67 g of CaO (cation to sugar mole ratio approximately 0.75:1) to 49.3 milliliters of deionized water resulted in the rapid formation of a rigid (light yellow) gel. The gel was subjected to mild heating and continuous mixing for approximatley 5–10 minutes. The redissolved gel was sprayed at high pressure (1000 psi) by means of a high pressure, low capacity, hydraulic nozzle into an open vessel containing liquid nitrogen. The fine droplets were instantaneously frozen and dispersed in the cryogen. The liquid nitrogen and frozen particle mixture was poured into freeze-drying trays. The trays were transferred to the freezedrying chamber and placed on already chilled (−40° C.) freeze-dryer shelves. The samples were freeze dried in accordance with Example 1.

The freeze dried calcium-fructose particles were observed to be a dry, free-flowing powder. These particles were found to be highly microporous and have a surface area of 225 $m^2/g$. The particles were exposed to the atmosphere for a period of 15 days and remained free-flowing as an essentially non-hygroscopic powder.

EXAMPLE 5

The addition of 20g of fructose to a CaO suspension which was prepared by adding 4.67g of CaO to 49.3 ml of water resulted in the formation of a rigid gel having a light yellow color. The gel was thoroughly mixed for approximately 5–10 minutes. The redissolved gel was sprayed under high pressure, approximately 1000 psi, by means of a high pressure, low capacity hydraulic nozzle into an open vessel containing 1480 ml of subambient (−60° C.) 200 proof ethanol (final ethanol to water ratio 30:1). The fine spray of droplets were quickly frozen and dehydrated upon contact with the ethanol. The calcium-fructose ethanol mixture was allowed to come to ambient temperature. Thereafter, the calcium-fructose particles were filtered from the ethanol, washed with an equivalent volume of fresh ethanol, filtered and placed in trays. The trays were transported to a vacuum oven and subjected to a vacuum of 100 Torr and a plate temperature of 50° C. overnight to remove any residual solvent. The calcium-fructose particles were perceived as a dry, free-flowing essentially non-hygroscopic and microporous powder possessing a surface area of 215 $m^2/g$.

EXAMPLE 6

An aqueous calcium-sucrose solution having a cation to sugar mole ratio of 0.55:1 and a total solids concentration of 33% by weight was prepared by adding 7.2g of CaO to an aqueous sucrose solution consisting of 80 g of sucrose and 174.4 ml. of water. The calcium-sucrose mixture was stirred until the solution cleared. The solution was sprayed at 1000 psi by means of a high-pressure, low capacity hydraulic nozzle into an open vessel containing liquid nitrogen. The liquid nitrogen and frozen particle mixture was poured into freeze drying trays. The trays were transferred to the freeze drying chamber and placed on the pre-chilled ($-40°$ C.) shelves. The liquid nitrogen was allowed to boil off leaving behind a flat bed of frozen spherical particles having a bed depth of approximately 1/8 to ¼ inches. The chamber was sealed and the product was subjected to vacuum of 10 micron Hg and an initial shelf temperature of $-35°$ C. Dry air was admitted to the chamber, at the end of the freeze drying cycle, to break the vacuum. The freeze dried product was found to be a light, free-flowing, non-hygroscopic powder having a surface area of 258 $m^2/g$. These particles were subjected to $CO_2$ adsorption-desorption analysis and found to adsorb approximately 34 cc/g of $CO_2$ gas at 30° C. of which about 32 cc/g can be attributed to chemical adsorption and 2-3 cc/g to physical adsorption.

EXAMPLE 7

An aqueous calcium-glucose solution having a cation to sugar mole ratio of 1:1 and a total solids concentration of 25% by weight was prepared by adding 6.23 g of CaO to an aqueous glucose solution consisting of 20 grams of glucose and 78.7 ml of water. The solution was continuously stirred for approximately 5-10 minutes. The calcium-glucose solution was sprayed, frozen, transferred and freeze dried all in accordance with Example 1.

The freeze dried calcium-glucose particles were observed to be dry, free-flowing and non hygroscopic. They were found to be highly microporous and have a surface area of 205 $m^2/g$.

While the foregoing describes a method for the manufacture of an improved microporous material by complexing a sugar with a metal cation salt, other cationic compounds and other edible materials come within the purview of the spirit and the scope of the claims when read with reference to the specification.

EXAMPLE 8

Microporous particles of calcium-sucrose having a surface area of 258 $m^2/g$, produced in accordance with the process of Example 6 were aromatized by contacting and combining the particles with orange oil at a level of about 10% by weight of the particles. The aromatized particles were then blended with a powdered, orange-flavored beverage mix at a level of 0.16% by weight, the mix by itself being essentially devoid of any aroma.

EXAMPLE 9

Microporous particles of calcium-sucrose were prepared using the steps of Example 6 and a solution having a calcium to sucrose mole ratio of 0.9:1 and a total solids concentration of 33% by weight. The solution was prepared by combining 50.7 grams of CaO, 342.3 grams of sucrose and 780 mls of water. The particles had a measured surface area of 274 $m^2/g$. These particles were loaded with orange oil and dry-blended with beverage mix as set forth in Example 8.

EXAMPLE 10

Identical amounts of the orange-oil-loaded particles of Examples 8, 9 were placed into stoppered 250 ml flasks. As a control an amount (250 micro-liters) of orange oil equal to the amount carried by the particles was placed in a third stoppered flask. All flasks were allowed to equilibrate for 24 hours at 30° C. Thereafter 1 cc samples of the headspace within the flasks were withdrawn and analyzed using standard gas chromatographic techniques. The control headspace sample registered $2.68 \times 10^6$ G.C. counts. Values for Example 8, 9 particles were $0.10 \times 10^6$ and $0.16 \times 10^6$ G.C. counts, respectively. As can be seen from the headspace aroma values more than 90% of the aroma is retained in the microporous salts, which retained aroma will be available for controlled evolution from the microporous salts to develop sequential headspace aromas (i.e., an in-use headspace aroma) to replace and replenish the aromas lost upon repeated openings and reclosing of the flask.

What is claimed is:

1. A method for producing a volatile flavor or aroma or gas-containing, microporous, non-hygroscopic, water-soluble cation-saccharide salt having a surface area of at least 10 $m^2/g$ comprising the steps of:
   (a) forming an aqueous solution of an inorganic compound and a water-soluble saccharide, said compound being present in an amount effective to raise the pH of the solution to between 9 and 14, and wherein the molar ratio of inorganic cation to saccharide is from about 0.5 to 1.5 moles of cation to 1.0 mole of saccharide;
   (b) providing conditions such that the inorganic compound dissociates to form a dissolved cation and dissolved anion and a saccharide-cation salt is formed, said salt being soluble in water and insoluble in alcohol;
   (c) spraying the saccharide-cation-containing solution of step (b) into a frigid, dehydrating solvent which quickly solidifies and dehydrates the spray droplets;
   (d) separating the solidified particles from the solvent; and thereafter,
   (e) loading the dried microporous particles of step (d) with sorbed gas or volatiles at from 0.1 to 20% by weight.

2. A method according to claim 1 wherein the cation is monovalent and is selected from the group consisting of Li, Na, K, Rb, Cs and combinations thereof.

3. A method according to claim 1 wherein the cation is divalent and is selected from the group consisting of Mg, Ca, Sr, Zn, Ba and combinations thereof.

4. A method according to claim 1 wherein the cation is trivalent and is selected from the group consisting of Al, Ce, La and combinations thereof.

5. A method according to claim 1 wherein the anion comprises an oxide, a hydroxide, or a carbonate.

6. A method according to claim 1 wherein the saccharide consists of monosaccharide, disaccharide, polysaccharide or mixtures thereof.

7. The method according to claim 1 wherein the solvent is an anhydrous alcohol having a temperature at or below $-60°$ C.

8. A method according to claim 1 wherein the mole ratio of cation to saccharide is about equimolar.

9. A method for producing a volatile flavor or aroma or gas-containing, microporous, non-hygroscopic water-soluble cation-saccharide salt having a surface area of at least 10 $m^2/g$ comprising the steps of:
   (a) forming an aqueous solution of an inorganic compound and a water-soluble saccharide, said compound being present in an amount effective to raise the pH of the solution to between 9 and 14, and wherein the molar ratio of inorganic cation to saccharide is from about 0.5 to 1.5 moles of cation to 1.0 mole of saccharide;

(b) providing conditions such that the inorganic compound dissociates to form a dissolved cation and dissolved anion and a saccharide-cation salt is formed, said salt being soluble in water and insoluble in alcohol;

(c) spraying the saccharide-cation-containing solution of step (b) into a liquid cryogen to quickly freeze the spray droplets;

(d) freeze drying the frozen spray droplets; and thereafter, (e) loading the dried microporous particles of step (d) with sorbed gas or volatiles at from 0.1 to 20% by weight.

10. The method according to claim 9 wherein the liquid cryogen is liquid nitrogen.

11. A method according to claim 9 wherein the cation is monovalent and is selected from the group consisting of Li, Na, K, Rb, Cs and combinations thereof.

12. A method according to claim 9 wherein the cation is divalent and is selected from the group consisting of Mg, Ca, Sr, Zn, Ba and combinations thereof.

13. A method according to claim 9 wherein the cation is trivalent and is selected from the group consisting of Al, Ce, La and combinations thereof.

14. A method according to claim 9 wherein the anion comprises an oxide, a hydroxide, or a carbonate.

15. A method according to claim 9 wherein the saccharide consists of monosaccharide, disaccharide, polysaccharide or mixtures thereof.

16. A method according to claim 9 wherein the mole ratio of cation to saccharide is about equimolar.

* * * * *